(12) United States Patent
Yonezawa et al.

(10) Patent No.: US 9,371,391 B2
(45) Date of Patent: Jun. 21, 2016

(54) ANTI-HUMAN IL-23 RECEPTOR ANTIBODY AND ENCODING POLYNUCLEOTIDES

(71) Applicant: Astellas Pharma Inc., Chuo-ku, Tokyo (JP)

(72) Inventors: Atsuo Yonezawa, Tokyo (JP); Makoto Ohori, Tokyo (JP); Takanori Sasaki, Tokyo (JP); Hiromu Sato, Tokyo (JP); Katsunari Taguchi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 14/381,268

(22) PCT Filed: Feb. 27, 2013

(86) PCT No.: PCT/JP2013/055082
§ 371 (c)(1),
(2) Date: Aug. 27, 2014

(87) PCT Pub. No.: WO2013/129454
PCT Pub. Date: Sep. 6, 2013

(65) Prior Publication Data
US 2015/0126713 A1    May 7, 2015

(30) Foreign Application Priority Data
Feb. 28, 2012   (JP) ................................ 2012-040958

(51) Int. Cl.
*C07K 16/28*    (2006.01)
*C12N 15/00*    (2006.01)

(52) U.S. Cl.
CPC ............ *C07K 16/2866* (2013.01); *C12N 15/00* (2013.01); *C07K 2317/24* (2013.01); *C07K 2317/33* (2013.01); *C07K 2317/73* (2013.01); *C07K 2317/76* (2013.01); *C07K 2317/92* (2013.01)

(58) Field of Classification Search
CPC ............ C07K 16/244; C07K 2317/24; C07K 2317/33; C07K 2317/73; C07K 2317/76; C07K 2317/92
See application file for complete search history.

(56) References Cited

FOREIGN PATENT DOCUMENTS

| EP | 2695897 A1 | 2/2014 |
|---|---|---|
| WO | 2008106134 A2 | 9/2008 |
| WO | 2010027767 A1 | 3/2010 |
| WO | 2010062663 A1 | 6/2010 |

OTHER PUBLICATIONS

Extended European Search Report, issued in EP Application No. 13754932.5, dated May 19, 2015.
International Search Report in PCT/JP2013/055082, mailed Apr. 2, 2013.
IPRP and Written Opinion of the International Search Authority in PCT/JP2013/055082, date of issuance Sep. 2, 2014.
EP Communication dated Apr. 21, 2016 for EP Application No. 13754932.5.

*Primary Examiner* — Robert Landsman
(74) *Attorney, Agent, or Firm* — Brinks Gilson & Lione

(57) ABSTRACT

[Problem]
An object of the present invention is to provide an anti-human IL-23R antibody having excellent activity and/or cross-reactivity compared to conventional IL-23R antibodies, and means for using the antibody to prevent or treat various diseases such as ophthalmic disease, inflammatory bowel disease, or psoriasis in which human IL-23R is involved in pathogenesis.
[Means for Solution]
An anti-human IL-23R antibody comprising a heavy-chain variable region consisting of the amino acid sequence shown by SEQ ID NO:10 or 14 and a light-chain variable region consisting of the amino acid sequence shown by SEQ ID NO:6 or 18.

25 Claims, No Drawings

ANTI-HUMAN IL-23 RECEPTOR ANTIBODY AND ENCODING POLYNUCLEOTIDES

TECHNICAL FIELD

The present invention relates to a novel anti-human IL-23 receptor antibody. Specifically, the novel anti-human IL-23 receptor antibody of the present invention has excellent activity and/or species cross-reactivity compared to conventional anti-human IL-23 receptor antibodies.

The sequence listing submitted to the USPTO on Aug. 27, 2014, in the ASCII text file "Y04-310190-KEN_US_Sequencelisting.txt", created Feb. 5, 2013, size 38KB, consisting of 25 sequences, is hereby incorporated by reference.

BACKGROUND ART

Interleukin-23 (also referred to as IL-23) is a cytokine produced by dendritic cells and the like, and is a heterodimeric cytokine consisting of two subunits, i.e., a p19 subunit which is a component specific for IL-23 and the p40 subunit which is also a component of IL-12 (non-patent document 1). IL-23 binds to the IL-23 receptor (also referred to as IL-23R) to transduce signals into cells (non-patent document 2). IL-23R is a heterodimeric receptor consisting of an IL-23R subunit and the IL-12Rβ1 subunit which is also a component of the IL-12 receptor. Also, it is known that the IL-12 receptor is a complex of an IL-12Rβ1 subunit and an IL-12Rβ1 subunit, and that IL-23 does not bind to the IL-12 receptor (non-patent document 1).

It is known that IL-23 is deeply involved in diseases, including psoriasis, inflammatory bowel disease (IBD) such as Crohn's disease (CD) or ulcerative colitis (UC), systemic lupus erythematosus (SLE), rheumatoid arthritis (RA), ankylosing spondylitis (AS), Behcet's disease, cancer, and ophthalmic diseases such as uveitis, dry eye, age-related macular degeneration, and ocular manifestation of Basedow's disease. Psoriasis is a chronic skin keratinization disorder and an increase in IL-23 expression in the skin of psoriasis patients has been observed (non-patent document 3).

Inflammatory bowel disease (IBD) is a chronic recurrent disease, which is represented by Crohn's disease (CD) or ulcerative colitis (UC), and causes deterioration in the function or structure of the digestive tract. It is known that lamina propria macrophages in the inflammatory sites of the intestinal tract of CD patients actively produce IL-23 (non-patent document 4), and it is considered that the lamina propria macrophages induce cytokines, including IL-21, IL-22 and IL-17, from immune cells and the like, to contribute to the inflammatory pathology of IBD (non-patent document 5).

Systemic lupus erythematosus (SLE) causes various symptoms to occur at various places over the entire body because of immune system stimulation, thus simultaneously or successively causing symptoms thought to be related to inflammation, including fever and systemic illness, as well as various symptoms which occur in joints, skin, intestinal organs, etc. It was reported that there is a positive correlation between the pathology of SLE and the number of IL-23R-positive T lymphocytes (non-patent document 6). Also, it is known that IL-23 in the blood of SLE patients is significantly higher than that in normal persons (non-patent document 7). This suggests that IL-23 is involved in SLE.

Ankylosing spondylitis (AS) is a chronic inflammatory disease that causes lesions mainly in the vertebra and sacroiliac joints. It is known that IL-23 in the blood of AS patients is significantly higher than that in normal persons, suggesting that IL-23 is involved in the pathology of AS (non-patent document 8).

Behcet's disease is a chronic inflammatory disease characterized by inflammation of the blood vessels of varying sizes, that is, vasculitis, and it is thought that an abnormality of the immune system and the activation of neutrophils are involved in the pathology. This recurrent abnormality in blood vessels can last for several days to several months, and can reoccur several times a year. In patients with Behcet's disease, IL-23 is significantly correlated with the activity of the disease, and the stimulation of IL-23 expression is observed in the serum of patients having uveitis, whose pathology is relating to that of Behcet's disease (non-patient document 9), suggesting that IL-23 is involved in this pathology.

Rheumatoid arthritis (RA) is a chronic autoimmune disease that causes deformation of joints and intense pain. IL-23 increases in the synovia and serum of RA patients (non-patient document 10), and the level of IL-23 in the serum of patients administered with a TNF blocker that is a drug for treating RA correlates with the degree of the pathology (non-patent document 11). Also, an anti-IL-23R antibody in the synovial membrane of RA patients inhibits the production of TNF-α and IL-6 (non-patent document 12), suggesting that IL-23 is involved in the pathology.

Uveitis, dry eye, age-related macular degeneration, and ocular manifestation of Basedow's disease are ophthalmic diseases in which inflammation is related. The expression of IL-23 protein or gene is increased in serum of Uveitis patient, conjunctival epithelium of dry eye patient, aqueous humor of age-related macular degeneration patient, and serum of patient affected with ocular manifestation of Basedow's disease (non-patent document 13, 14, 15, 16), suggesting that IL-23 is involved in these pathology.

Regarding cancer, IL-23 is relating to growth and progression of cancer (non-patent document 17), and in IL-23-deficient mouse with grafted cancer, the progression of the cancer is suppressed (non-patent document 18). These suggests that IL-23 is involved in the pathology.

Thus, when a monoclonal antibody that has an activity of binding specifically to the IL-23R to inhibit various actions of IL-23 can be developed, it is expected to be useful for the treatment, prevention or diagnosis of various diseases in which IL-23 is involved in disease pathology.

Antibodies that have been studied to date and which have been reported to exhibit the effect of inhibiting the function of the human IL-23R include the mouse monoclonal antibody m20D7 (patent document 1) or its humanized monoclonal antibody hum20D7 (patent document 1), the rat monoclonal antibody 8B10 (patent document 1) or its humanized monoclonal antibody (patent document 2). Among them, hum20D7 has been reviewed in the most detail, and the effect thereof on actual cell responses became clear from the results of experiments based on the inhibition of signaling of Kit 225 cells that are established cultured cells expressing the IL-23 receptor.

However, conventional antibodies do not appear to have a sufficient neutralizing activity for IL-23 signaling in cells from the viewpoint of effectiveness.

Main factors that determine the effective dosage of an antibody drug include antibody activity to inhibit ligand-receptor binding and the amount of antigen present in the body. An increase in the activity of an antibody to inhibit the binding appears to be a very beneficial improvement that leads to a decrease in the dosage of the antibody, resulting in a decrease in the financial burden or medical expenses of patients. Also, even if an antibody has a high binding activity for an antigen (a ligand, a receptor, etc.), this does not mean that the antibody can highly exhibit the desired neutralizing activity. This is because the antibody should occupy a suitable site in an antigen in order for the antibody to strongly inhibit the ligand-receptor binding. In other words, the strength of the neutralizing activity of the antibody is important when evaluating the effect of the antibody drug.

Also, the safety evaluation using animals is very important in the development of medical drugs. The international guideline ICH-S6 related to the development of medical drugs includes the following description: "Safety evaluation programs should normally include two relevant species. However, in certain justified cases one relevant species may suffice (e.g., when only one relevant species can be identified or where the biological activity of the biopharmaceutical is well understood).". As described above, in the development of medical drugs, testing on one or more kinds of animal species other than humans is required; however, in order to carry out a test on animal species when developing an antibody drug, the antibody is required to have cross-reactivity with antigens derived from animal species other than humans. However, it is generally not easy to obtain a monoclonal antibody that has high selectivity and maintains high activity while displaying species cross-reactivity.

Therefore, obtaining a anti-human IL-23 receptor antibody which has strong neutralizing activity compared to conventional antibodies and shows species cross-reactivity is required for use in the treatment, prevention or diagnosis of various diseases by administering the antibody to humans.

RELATED ART

Patent Document

[Patent document 1] WO2008/106134
[Patent document 2] WO2010/027767

Non-Patent Document

[Non-patent document 1] Oppmann B et al, Immunity. 2000 November; 13(5): 715-25
[Non-patent document 2] Parham C et al, J Immunol. 2002 June 1; 168(11): 5699-708
[Non-patent document 3] Lee E et al, J Exp Med. 2004 Jan 5; 199(1): 125-30
[Non-patent document 4] Kamada N et al, J Clin Invest. 2008; 118: 2269-2280
[Non-patent document 5] Sarra M et al, Inflamm Bowel Dis. 2010 October; 16(10): 1808-1813
[Non-patent document 6] Puwipirom H et al, Arthritis Res Ther. 2010 November 29; 12(6): R215
[Non-patent document 7] Mok M Y et al, J Rheumatol. 2010 October; 37(10): 2046-52
[Non-patent document 8] Mei Y et al, Clin Rheumatol. 2011 February; 30(2): 269-73
[Non-patent document 9] Habibagahi Z et al, Mod Rheumatol. 2010 April; 20(2): 154-9
[Non-patent document 10] Kim H R et al, Rheumatology (Oxford). 2007 January; 46(1): 57-6
[Non-patent document 11] Kageyama Y et al, Rheumatol Int. 2007 December; 28(2): 137-43
[Non-patent document 12] Hillyer P et al, Rheumatology (Oxford). 2009 December; 48(12): 1581-9
[Non-patent document 13] Chi W et al, Invest Ophthalmol Vis Sci. 2008 July; 49(7): 3058-64.
[Non-patent document 14] De Paiva C S et al, Mucosal Immunol. 2009 May; 2(3): 243-53.

[Non-patent document 15] Sasaki S et al, Invest Ophthalmol Vis Sci. 2012 Jun. 5; 53(7): 3424-30.
[Non-patent document 16] Kim S E et al, Graefes Arch Clin Exp Ophthalmol. 2012 October; 250(10): 1521-6.
[Non-patent document 17] Grivennikov S I et al, Nature. 2012 Nov. 8; 491(7423): 254-8.
[Non-patent document 18] Langowski J L et al, Nature. 2006 Jul. 27; 442(7101): 461-5.

DISCLOSURE OF INVENTION

Problem to Be Solved by the Invention

An object of the present invention is to provide anti-human IL-23R antibodies having excellent activity and/or species cross-reactivity compared to conventional anti-human IL-23R antibodies.

Means for Solving the Problems

Accordingly, the present invention includes the following inventions as medically or industrially useful substances and methods.

(1) An anti-human IL-23R antibody selected from any one of the following 1) to 4):

1) an anti-human IL-23R antibody comprising a heavy-chain variable region consisting of the amino acid sequence shown by SEQ ID NO:10 and a light-chain variable region consisting of the amino acid sequence shown by SEQ ID NO:18;

2) an anti-human IL-23R antibody comprising a heavy-chain variable region consisting of the amino acid sequence shown by SEQ ID NO:10 and a light-chain variable region consisting of the amino acid sequence shown by SEQ ID NO:6;

3) an anti-human IL-23R antibody comprising a heavy-chain variable region consisting of the amino acid sequence shown by SEQ ID NO:14 and a light-chain variable region consisting of the amino acid sequence shown by SEQ ID NO:6; and 4) an anti-human IL-23R antibody comprising a heavy-chain variable region consisting of the amino acid sequence shown by SEQ ID NO:14 and a light-chain variable region consisting of the amino acid sequence shown by SEQ ID NO:18.

(2) The anti-human IL-23R antibody of (1) above, comprising the heavy-chain variable region consisting of the amino acid sequence shown by SEQ ID NO:10 and the light-chain variable region consisting of the amino acid sequence shown by SEQ ID NO:18.

(3) The anti-human IL-23R antibody of (1) above, comprising the heavy-chain variable region consisting of the amino acid sequence shown by SEQ ID NO:10 and the light-chain variable region consisting of the amino acid sequence shown by SEQ ID NO:6.

(4) The anti-human IL-23R antibody of (1) above, comprising the heavy-chain variable region consisting of the amino acid sequence shown by SEQ ID NO:14 and the light-chain variable region consisting of the amino acid sequence shown by SEQ ID NO:6.

(5) The anti-human IL-23R antibody of (1) above, comprising the heavy-chain variable region consisting of the amino acid sequence shown by SEQ ID NO:14 and the light-chain variable region consisting of the amino acid sequence shown by SEQ ID NO:18.

(6) The anti-human IL-23R antibody of any one of (1) to (5) above, wherein the heavy-chain constant region of the antibody is a human Igγ1 constant region.

(7) The anti-human IL-23R antibody of any one of (1) to (5) above, wherein the light-chain constant region of the antibody is a human Igκ constant region.

(8) The anti-human IL-23R antibody of any one of (1) to (5) above, wherein the heavy-chain constant region of the antibody is a human Igγ1 constant region, and the light-chain constant region of the antibody is a human Igκ constant region.

(9) The anti-human IL-23R antibody of (2) above, comprising a heavy chain consisting of the amino acid sequence shown by SEQ ID NO:12 and a light chain consisting of the amino acid sequence shown by SEQ ID NO:20.

(10) The anti-human IL-23R antibody of (3) above, comprising a heavy chain consisting of the amino acid sequence shown by SEQ ID NO:12 and a light chain consisting of the amino acid sequence shown by SEQ ID NO:8.

(11) The anti-human IL-23R antibody of (4) above, comprising a heavy chain consisting of the amino acid sequence shown by SEQ ID NO:16 and a light chain consisting of the amino acid sequence shown by SEQ ID NO:8.

(12) The anti-human IL-23R antibody of (5) above, comprising a heavy chain consisting of the amino acid sequence shown by SEQ ID NO:16 and a light chain consisting of the amino acid sequence shown by SEQ ID NO:20.

(13) A polynucleotide comprising a sequence encoding the heavy-chain variable region of the antibody of any one of (1) to (12) above.

(14) A polynucleotide comprising a sequence encoding the light-chain variable region of the antibody of any one of (1) to (12) above.

(15) An expression vector comprising the polynucleotide of (13) and/or (14) above.

(16) A host cell transformed with the expression vector of (15) above.

(17) The host cell of (16) above, wherein the host cell is selected from the group consisting of the following (a) and (b):

(a) a host cell transformed with an expression vector comprising a polynucleotide comprising a sequence that encodes the heavy-chain variable region of the antibody of any one of (1) to (12) above and a polynucleotide comprising a sequence that encodes the light-chain variable region of the antibody; and (b) a host cell transformed with an expression vector comprising a polynucleotide comprising a sequence that encodes the heavy-chain variable region of the antibody of any one of (1) to (12) above and an expression vector comprising a polynucleotide comprising a sequence that encodes the light-chain variable region of the antibody.

(18) A method for producing the anti-human IL-23R antibody of any one of (1) to (12) above, the method comprising a step of culturing the host cell of (16) or (17) above and expressing the anti-human IL-23R antibody.

(19) An agent for treating ophthalmic disease, inflammatory bowel disease, or psoriasis, comprising the anti-human IL-23R antibody of any one of (1) to (12) above.

(20) A method for preventing or treating ophthalmic disease, inflammatory bowel disease, or psoriasis, comprising a step of administering a therapeutically effective amount of the anti-human IL-23R antibody of any one of (1) to (12) above.

(21) The anti-human IL-23R antibody of any one of (1) to (12) above, for use in preventing or treating ophthalmic disease, inflammatory bowel disease, or psoriasis.

Effects of the Invention

The present invention provides anti-human IL-23R antibodies having excellent activity and/or species cross-reactivity compared to conventional anti-human IL-23R antibodies. The anti-human IL-23R antibodies of the present invention have a potent effect of suppressing immune cells by inhibiting the function of human IL-23R, and are useful for preventing or treating various diseases in which human IL-23 is involved in disease pathology. Also, such anti-human IL-23R antibodies of the present invention provide superior improvements in clinical applications such as reduction of dosage, extension of administration interval, improvement of the mode of administration (e.g., a subcutaneous injection) and the like, and greatly contribute to the treatment effectiveness and improvement in patient compliance. In addition, the antibodies have species cross-reactivity with antigens derived from animals (particularly animals that are used in the development of medical drugs) other than humans, and thus enable safety tests to be carried out using animals that are required to develop the antibody into a medical drug. Thus, the antibodies greatly contribute to ensuring the safety of humans administered therewith.

EMBODIMENTS FOR CARRYING OUT THE INVENTION

Hereinafter, the present invention will be described in detail.

The present inventors have demonstrated considerable ingenuity and consideration for the production of an anti-human IL-23R antibody and, as a result, succeeded in producing an anti-human IL-23R antibody having excellent activity and/or species cross-reactivity compared to conventional anti-human IL-23R antibodies.

The basic structure of an antibody molecule is shared amongst all antibody classes, and is configured with a heavy chain having a molecular weight of 50000 to 70000 and a light chain having a molecular weight of 20000 to 30000. The heavy chain usually consists of a polypeptide chain comprising about 440 amino acids. Heavy chains have structures characteristic of different classes, and are called the γ, μ, α, δ, and ε chains corresponding to IgG, IgM, IgA, IgD, and IgE. Furthermore, IgG occurs as IgG1, IgG2, IgG3, and IgG4, and the corresponding chains are called γ1, γ2, γ3, and γ4, respectively. A light chain usually consists of a polypeptide chain comprising about 220 amino acids, two types of which, type L and type K, are known, and are called the λ and κ chains, respectively. Regarding the peptide configuration of the basic structure of an antibody molecule, two homologous heavy chains and two homologous light chains are bound via disulfide bonds (S—S bonds) and non-covalent bonds, and the molecular weight is 150000 to 190000. The two kinds of light chains are capable of pairing with any heavy chain. Each antibody molecule always consists of two identical light chains and two identical heavy chains.

There are four intrachain S—S bonds in a heavy chain (five bonds for μ and ε chains) and two in a light chain; one loop is formed per 100 to 110 amino acid residues, and this steric structure is alike among the loops, and is called a structural unit or domain. For both heavy chains and light chains, the amino acid sequence of the domain located at the N terminus thereof is not constant, even in a reference standard from the same class (subclass) of the same animal species, and this domain is called the variable region. Each of the domains is called a heavy-chain variable region ($V_H$) and a light-chain variable region ($V_L$), respectively. The amino acid sequence on the C-terminal side therefrom is nearly constant in each class or subclass, and is called a constant region (each of the domains is called $C_H1$, $C_H2$, $C_H3$ and $C_L$, respectively).

The antigenic determinant site of an antibody is configured with $V_H$ and $V_L$, and the binding specificity depends on the amino acid sequence of this site. On the other hand, biological activities such as binding to complements or various cells reflect the differences in the constant region structure among the various classes of Ig. The variability in the variable regions of the light chain and heavy chains is mostly limited to three small hypervariable regions existing in both chains, and these regions are called complementarity determining regions (CDRs; CDR1, CDR2 and CDR3 starting from the N-terminal side). The remaining portion of the variable region is called a framework region (FR) and is relatively constant.

The inventive anti-human IL-23R antibody successfully constructed by the present inventors is an anti-human IL-23R antibody having any one of the following features:

1) An anti-human IL-23R antibody comprising a heavy-chain variable region consisting of the amino acid sequence shown by SEQ ID NO:10 and a light-chain variable region consisting of the amino acid sequence shown by SEQ ID NO:18.

2) An anti-human IL-23R antibody comprising a heavy-chain variable region consisting of the amino acid sequence shown by SEQ ID NO:10 and a light-chain variable region consisting of the amino acid sequence shown by SEQ ID NO:6.

3) An anti-human IL-23R antibody comprising a heavy-chain variable region consisting of the amino acid sequence shown by SEQ ID NO:14 and a light-chain variable region consisting of the amino acid sequence shown by SEQ ID NO:6.

4) An anti-human IL-23R antibody comprising a heavy-chain variable region consisting of the amino acid sequence shown by SEQ ID NO:14 and a light-chain variable region consisting of the amino acid sequence shown by SEQ ID NO:18.

Specifically, the present inventors constructed antibodies using a human monoclonal antibody development technology, "VelocImmune" mouse [VelocImmune antibody technology; Regeneron Inc. (U.S. Pat. No. 6,596,541)], and screened the antibodies using tests for various biological activities and physical properties, thereby succeeding in identifying the anti-human IL-23R antibody of the present invention. In the VelocImmune technology, transgenic mice in which the endogenous immunoglobulin heavy chain and light chain variable regions are replaced with the corresponding human variable regions are challenged with the antigen of interest (for example, human IL-23R), and lymphatic cells are recovered from the mice that express antibodies. The lymphatic cells are fused with mouse myeloma cells to prepare hybridomas. The hybridoma cells are screened to identify hybridoma cells that produce those antibodies that specifically bind to the antigen of interest. The antibodies that are produced herein are antibodies having the variable regions of human antibodies and the constant regions of mouse antibodies (also referred to as chimeric antibodies). Then, if the antibody that binds specifically to the antigen of interest are identified, DNAs that encode the variable regions of the heavy chain and light chain of the antibody are isolated from the hybridoma cells and linked to DNAs encoding the constant regions of the heavy chain and light chain of a desired class of human antibody, respectively. The resulting DNA encoding the heavy chain and light chain of the antibody is expressed in cells (e.g., CHO cells) to produce an antibody molecule. The heavy chain and light chain of the antibody produced by the above method are the heavy chain and light chain of a "fully human" antibody derived from a human immunoglobulin gene.

The anti-human IL-23R antibody of the present invention can be easily prepared by those skilled in the art on the basis of the sequence information on the heavy-chain variable region and light-chain variable region thereof disclosed herein, using a method commonly known in the art. Preferably, the anti-human IL-23R antibody of the present invention can be prepared as a fully human antibody by linking the heavy chain variable region and light chain variable region thereof to the heavy chain constant region and light chain constant region of a human antibody, respectively. Specifically, a heavy-chain variable region gene fragment having a base sequence that encodes the amino acid sequence of the heavy-chain variable region of the antibody of the present invention (SEQ ID NO:10 or SEQ ID NO:14), and a light-chain variable region gene fragment having a base sequence that encodes the amino acid sequence of the light-chain variable region of the antibody of the present invention (SEQ ID NO:6 or SEQ ID NO:18) are prepared. Then, the variable region genes are linked to a constant region gene in an appropriate class of human antibody to prepare a fully human antibody gene. Next, this antibody gene is linked to an appropriate expression vector and introduced into a cultured cell. Finally, this cultured cell is cultured, whereby a monoclonal antibody can be obtained from the culture supernatant.

The each gene fragment having base sequence encoding the amino acid sequence of the heavy-chain variable region and the light-chain variable region of the antibody of the present invention can be synthesized using a gene synthesis method known in the art, on the basis of, for example, base sequences designed based on the amino acid sequences of the heavy chain variable region and light chain variable region. Examples of this gene synthesis method include various methods known to those skilled in the art, such as the antibody gene synthesis method described in WO90/07861. Also, once the variable region gene fragment of the antibody of the present invention is obtained, a mutation can be introduced into the specified site of the gene fragment, thereby obtaining the other antibodies of the present invention. Examples of the method for introducing the mutation include various methods known to those skilled in the art, such as site-directed mutagenesis (Current Protocols in Molecular Biology edit. Ausubel et al. (1987) Publish. John Wiley & Sons Section 8.1-8.5).

Then, the above-described variable region gene fragments are linked to the constant region gene of the human antibody to prepare a fully human antibody gene. Although any subclass of the constant region (for example, the constant region of γ1, γ2, γ3 or γ4 for heavy chain or the constant region of λ or κ chain for light chain) can be chosen as the constant region of the human antibody used, human Igγ1 as the heavy-chain constant region, and human Igκ as the light-chain constant region, can preferably be used.

Subsequent to the preparation of this fully human antibody gene, introduction of the antibody gene into an expression vector, introduction of the expression vector into cultured cells, cultivation of the cultured cells, purification of the antibody and the like can be performed using various methods known in the art.

Examples of the expression vector that is linked to the antibody gene thus obtained include GS vector pEE6.4 or pEE12.4 (Lonza Biologics), but are not specifically limited, so long as they can express an antibody gene. Also, the variable region gene fragment above may be introduced into an expression vector already having a human Ig constant region gene such as AG-γ1 or AG-κ (for example, see WO94/20632) to express the antibody gene.

The above-described expression vector is introduced into cultured cells by, for example, a calcium phosphate method or an electroporation method and the like.

Examples of the cultured cells into which the expression vector is introduced include cultured cells such as CHO-K1SV cells, CHO-DG44 cells and 293 cells, and these cells may be cultured by a conventional method.

After the above-described culture, the antibody accumulated in the culture supernatant can be purified by various column chromatography, for example, various column chromatographic processes using a Protein A or protein G column.

The anti-human IL-23R antibody of the present invention is an antibody binding to human IL-23R. Examples of a method for measuring the binding activity of the obtained anti-human IL-23R antibody for human IL-23R include methods such as ELISA (Enzyme linked immunosorbent assay) or FACS (Fluorescence-activated cell sorting). For example, when ELISA is used, a fusion protein of the extracellular domain of human IL-23R (SEQ ID NO:1) and immunoglobulin Fc is immobilized onto an ELISA plate, and the anti-human IL-23R antibody is added thereto, and allowed to react therewith. Then, the fusion protein is allowed to react with secondary antibody such as an anti-IgG antibody labeled with an enzyme such as horseradish peroxidase (HRP), and washed. Then, the activity is measured using an activity-detecting reagent [for example, a BM-chemiluminescence ELISA substrate (POD) (Roche Diagnostics) when an HRP label is used] or the like, thereby confirming the binding of the secondary antibody. In addition, the species cross-reactivity of the anti-human IL-23R antibody of the present invention may be evaluated by using IL-23Rs derived from other animals (for example, monkey IL-23R) to measure the binding activity for them.

Furthermore, the anti-human IL-23R antibody of the present invention has neutralizing activity against human IL-23R. As used herein, the "neutralizing activity" of the antibody means an activity to inhibit any biological activity resulting from IL-23R by binding to IL-23R, and can be evaluated on one or more biological activities of IL-23R as an index. Examples of such neutralizing activity include the activity of inhibiting the proliferation of Kit 225 cells that are IL-23R responsive cells, and the activity of inhibiting human IL-23-stimulated STAT3 phosphorylation, and the neutralizing activity can be evaluated using a method as described in the examples below.

Examples of methods for various stabilities (for example, thermal stability, long-term storage stability and high-concentration stability) of the anti-human IL-23R antibody include differential scanning calorimetry or a method of measuring the formation of aggregates during antibody storage.

Preferably, the anti-human IL-23R antibody of the present invention can be easily obtained by synthesizing DNA comprising a base sequence encoding the heavy-chain variable region amino acid sequence shown by SEQ ID NO:10 or 14 and DNA comprising a base sequence encoding the light-chain variable region amino acid sequence shown by SEQ ID NO:6 or 18, and linking the DNAs to a suitable class of human antibody constant region genes, preferably a human Igγ1 constant region gene for the heavy chain and a human Igκ constant region gene for the light chain, to construct a fully human antibody gene by using a method known in the art, and introducing the fully human antibody gene into an expression vector, introducing the expression vector into a cultured cell, culturing the cultured cell, and purifying an antibody harvested from the cultured cell by using various methods known in the art. Preferably, DNA comprising a base sequence encoding the heavy-chain variable region amino acid sequences shown by SEQ ID NO:10 or 14 comprises the base sequences shown by SEQ ID NO:9 or 13, respectively. Preferably, DNA comprising a base sequence encoding the light-chain variable region amino acid sequences shown by SEQ ID NO:6 or 18 comprises the base sequences shown by SEQ ID NO:5 or 17, respectively.

A preferred anti-human IL-23R antibody heavy-chain of the present invention, comprising the heavy-chain variable region shown by SEQ ID NO:10 and a human Igγ1 constant region, is a heavy chain consisting of the amino acid sequence shown by SEQ ID NO:12. A preferred anti-human IL-23R antibody light-chain of the present invention, comprising the light-chain variable region shown by SEQ ID NO:18 and a human Igκ constant region, is a light chain consisting of the amino acid sequence shown by SEQ ID NO:20. Preferably, DNA comprising a base sequence encoding an anti-human IL-23R antibody heavy-chain consisting of the amino acid sequence shown by SEQ ID NO:12 comprises the base sequence shown by SEQ ID NO:11. Preferably, DNA comprising a base sequence encoding an anti-human IL-23R antibody light-chain consisting of the amino acid sequence shown by SEQ ID NO:20 comprises the base sequence shown by SEQ ID NO:19. Examples of the anti-human IL-23R antibody of the present invention, which comprises a heavy chain consisting of the amino acid sequence shown by SEQ ID NO:12 and a light chain consisting of the amino acid sequence shown by SEQ ID NO:20, include a fully human 25-3-2 antibody as described in examples below.

A preferred anti-human IL-23R antibody heavy-chain of the present invention, comprising the heavy-chain variable region shown by SEQ ID NO:10 and a human Igγ1 constant region, is a heavy chain consisting of the amino acid sequence shown by SEQ ID NO:12. A preferred anti-human IL-23R antibody light-chain of the present invention, comprising the light-chain variable region shown by SEQ ID NO:6 and a human Igκ constant region, is a light chain consisting of the amino acid sequence shown by SEQ ID NO:8. Preferably, DNA comprising a base sequence encoding an anti-human IL-23R antibody heavy-chain consisting of the amino acid sequence shown by SEQ ID NO:12 comprises the base sequence shown by SEQ ID NO:11. Preferably, DNA comprising a base sequence encoding an anti-human IL-23R antibody light-chain consisting of the amino acid sequence shown by SEQ ID NO:8 comprises the base sequence shown by SEQ ID NO:7. Examples of the anti-human IL-23R antibody of the present invention, which comprises a heavy chain consisting of the amino acid sequence shown by SEQ ID NO:12 and a light chain consisting of the amino acid sequence shown by SEQ ID NO:8, include a fully human 25-3-1 antibody as described in the examples below.

A preferred anti-human IL-23R antibody heavy-chain of the present invention, comprising the heavy-chain variable region shown by SEQ ID NO:14 and a human Igγ1 constant region, is a heavy chain consisting of the amino acid sequence shown by SEQ ID NO:16. A preferred anti-human IL-23R antibody light-chain of the present invention, comprising the light-chain variable region shown by SEQ ID NO:6 and a human Igκ constant region, is a light chain consisting of the amino acid sequence shown by SEQ ID NO:8. Preferably, DNA comprising a base sequence encoding an anti-human IL-23R antibody heavy-chain consisting of the amino acid sequence shown by SEQ ID NO:16 comprises the base sequence shown by SEQ ID NO:15. Preferably, DNA comprising a base sequence encoding an anti-human IL-23R antibody light-chain consisting of the amino acid sequence shown by SEQ ID NO:8 comprises the base sequence shown by SEQ ID NO:7. Examples of the anti-human IL-23R antibody of the present invention, which comprises a heavy chain consisting of the amino acid sequence shown by SEQ ID NO:16 and a light chain consisting of the amino acid sequence shown by SEQ ID NO:8, include a fully human 25-3-3 antibody as described in examples below.

A preferred anti-human IL-23R antibody heavy-chain of the present invention, comprising the heavy-chain variable region shown by SEQ ID NO:14 and a human Igγ1 constant region, is a heavy chain consisting of the amino acid sequence shown by SEQ ID NO:16. A preferred anti-human IL-23R antibody light-chain of the present invention, comprising the light-chain variable region shown by SEQ ID NO:18 and a human Igκ constant region, is a light chain consisting of the amino acid sequence shown by SEQ ID NO:20. Preferably, DNA comprising a base sequence encoding an anti-human IL-23R antibody heavy-chain consisting of the amino acid sequence shown by SEQ ID NO:16 comprises the base sequence shown by SEQ ID NO:15. Preferably, DNA comprising a base sequence encoding an anti-human IL-23R antibody light-chain consisting of the amino acid sequence shown by SEQ ID NO:20 comprises the base sequence shown by SEQ ID NO:19. Examples of the anti-human IL-23R antibody of the present invention, which comprises a heavy chain consisting of the amino acid sequence shown by SEQ ID NO:16 and a light chain consisting of the amino acid sequence shown by SEQ ID NO:20, include a fully human 25-3-4 antibody as described in the examples below.

The present invention also comprises anti-human IL-23R antibody fragments such as a single-chain variable region fragment (scFv), Fab, Fab' and F(ab')$_2$, which comprise the heavy-chain variable region and light-chain variable region of the antibody of the present invention and maintain the activity of the antibody. Any person skilled in the art can construct a fusion antibody of the anti-human IL-23R antibody or antibody fragment and another peptide or protein and can also construct a modified antibody having a modifying agent bound thereto, on the basis of the present invention. The other peptide or protein used for the fusion is not specifically limited, so long as it does not reduce the binding activity of the antibody; examples thereof include human serum albumin, various tag peptides, artificial helix motif peptide, maltose-binding proteins, glutathione S transferase, various toxins, other peptides or proteins capable of promoting multimerization, and the like. The modifying agent used for the modification is not specifically limited, so long as it does not reduce the binding activity of the antibody; examples thereof include polyethylene glycol, sugar chains, phospholipids, liposomes, low-molecular compounds and the like.

The inventive anti-human IL-23R antibody thus obtained may further be purified as required, and then may be formulated according to a conventional method. It may be used for the treatment of diseases, including psoriasis, rheumatoid arthritis, systemic lupus erythematosus (SLE), inflammatory bowel disease (IBD) such as Crohn's disease or ulcerative colitis, ankylosing spondylitis (AS), Behcet's disease, cancer, and ophthalmic diseases such as uveitis, dry eye, age-related macular degeneration, and ocular manifestation of Basedow's disease and the like, in which IL-23R is involved in disease pathology.

The anti-human IL-23R antibody of the present invention may preferably be used as an agent for treating ophthalmic disease, inflammatory bowel disease, or psoriasis. Examples of the formulation of this treating agent and the like include parenteral formulations such as injectable agents, infusion agents, and eye-drops, which are preferably administered by intravenous administration, subcutaneous administration, intraocular administration, eye-drops administration and the like. In the formulation process, carriers or additives that match these formulations can be used within a pharmaceutically acceptable range.

The amount of inventive anti-human IL-23R antibody added in the above-described formulation varies depending on the patient's symptom severity or age, the dosage form of the formulation used or the binding titer of the antibody and the like; for example, about 0.001 mg/kg to 100 mg/kg of the antibody may be used.

The present invention also provides a polynucleotide comprising a sequence encoding the anti-human IL-23R antibody of the present invention, and an expression vector comprising the same. The present invention also provides a polynucleotide comprising a sequence encoding the heavy chain variable region of the anti-human IL-23R antibody of the present invention, and a polynucleotide comprising a sequence encoding the light chain variable region of the anti-human IL-23R antibody of the present invention, and an expression vector comprising either or both of them. The expression vector of the present invention is not specifically limited, so long as it can express a gene that encodes the antibody of the present invention or its heavy-chain variable region and/or light-chain variable region in various host cells of prokaryotic cells and/or eukaryotic cells, and produce these polypeptides. Examples thereof include plasmid vectors, viral vectors (for example, adenovirus, retrovirus) and the like. Preferably, the expression vector of the present invention comprises a polynucleotide comprising either a sequence encoding the heavy chain or light chain of the above-described antibody of the present invention, or both a polynucleotide comprising a sequence encoding the heavy chain of the antibody of the present invention and a polynucleotide comprising a sequence encoding the light chain of the antibody of the present invention.

The expression vector of the present invention can comprise a promoter operably linked to the gene that encodes the anti-human IL-23R antibody of the present invention or the heavy chain variable region and/or the light chain variable region thereof. Examples of a promoter for expressing a gene encoding the antibody of the present invention or the heavy chain variable region and/or the light chain variable region thereof in a bacterium include Trp promoter, lac promoter, recA promoter, λPL promoter, lpp promoter, tac promoter and the like, when the host is a bacterium of the genus *Escherichia*. Examples of a promoter for expression in yeast include PHO5 promoter, PGK promoter, GAP promoter and ADH promoter, and some examples of a promoter for expression in the genus *Bacillus* include SL01 promoter, SP02 promoter, penP promoter and the like. When the host is a eukaryotic cell such as a mammalian cell, examples of the promoter include SV40-derived promoter, retrovirus promoter, heat shock promoter and the like.

When a bacterium, particularly *Escherichia coli*, is used as the host cell, the expression vector of the present invention can further comprise an initiation codon, a stop codon, a terminator region and a replicable unit. When yeast, an animal cell or insect cell is used as the host, the expression vector of the present invention can comprise an initiation codon and a stop codon. In this case, it may comprise an enhancer sequence, noncoding regions on the 5' side and 3' side of a gene that encodes the antibody of the present invention or the heavy chain variable region or light chain variable region thereof, a secretion signal sequence, a splicing junction, a polyadenylation region, a replicable unit or the like. Also, it may comprise a selection marker that is in common use (for example, tetracycline-resistant gene, ampicillin-resistant gene, kanamycin-resistant gene, neomycin-resistant gene, dihydrofolic acid reductase gene) according to the intended use.

The present invention also provides a transformant introduced with a gene encoding the antibody of the present invention or a gene encoding the heavy chain variable region of the antibody of the present invention and/or the light chain variable region of the antibody of the present invention. Such a transformant can be prepared by, for example, transforming a host cell with the expression vector of the present invention. A host cell that is used to prepare the transformant is not specifically limited, so long as it is suitable for the aforementioned expression vector and is transformable; examples thereof include various cells such as natural cells or artificially established lines of cells commonly being used in the technical field of the present invention (for example, bacteria (bacteria of the genus *Escherichia*, bacteria of the genus *Bacillus*), yeasts (the genus *Saccharomyces*, the genus *Pichia* and the like), animal cells or insect cells (for example, Sf9) and the like. The transformation can be performed by any known method per se.

Preferably, the transformant of the present invention is either a host cell transformed with an expression vector comprising a polynucleotide comprising a sequence encoding the heavy chain variable region of the antibody of the present invention and a polynucleotide comprising a sequence encoding the light chain variable region of the antibody of the present invention, or a host cell transformed with an expression vector comprising a polynucleotide comprising a sequence encoding the heavy chain variable region of the antibody of the present invention and an expression vector comprising a polynucleotide comprising a sequence encoding the light chain variable region of the antibody of the present invention. More preferably, the transformant of the present invention is a host cell transformed with an expression vector comprising a polynucleotide comprising a sequence encoding the heavy chain of the above-described antibody of the present invention and a polynucleotide comprising a sequence encoding the light chain of the antibody of the present invention, or a host cell transformed with an expression vector comprising a polynucleotide comprising a sequence encoding the heavy chain of the above-mentioned antibody of the present invention and an expression vector comprising a polynucleotide comprising a sequence encoding the light chain of the antibody of the present invention.

The present invention also provides a method for producing the anti-human IL-23R antibody of the present invention, the method comprising expressing in a host cell a gene encoding the antibody of the present invention or a gene encoding the heavy chain variable region of the antibody of the present invention and/or a gene encoding the light chain variable region of the antibody of the present invention, that is, using such a transformant. Preferably, the host cell that is used in the above method is a host cell transformed with the above-described expression vector of the present invention, and the expression vector may separately or simultaneously comprise a polynucleotide comprising a sequence encoding the heavy chain variable region of the antibody of the present invention and a polynucleotide comprising a sequence encoding the light chain variable region of the antibody of the present invention.

When producing the anti-human IL-23R antibody of the present invention, the transformant may be cultured in a nutrient medium. The nutrient medium preferably contains a carbon source and an inorganic nitrogen source or organic nitrogen source, which are required for the growth of the transformant. Examples of the carbon source include glucose, dextran, soluble starch, sucrose and the like; examples of the inorganic nitrogen source or organic nitrogen source include ammonium salts, nitrates, amino acids, corn steep liquor, peptone, casein, meat extract, soybean cake, potato extract and the like. If desired, other nutrients (for example, inorganic salts (for example, calcium chloride, sodium dihydrogen phosphate, magnesium chloride), vitamins, antibiotics (for example, tetracycline, neomycin, ampicillin, kanamycin and the like) and the like) may be contained.

Culture of the transformant is performed by a method known per se. Culture conditions, for example, temperature, pH of the medium, and culture time are suitably selected. For example, when the host is an animal cell, an MEM medium (Science, Vol. 122, p. 501, 1952), DMEM medium (Virology, Vol. 8, p. 396, 1959), RPMI1640 medium (J. Am. Med. Assoc., Vol. 199, p. 519, 1967), 199 medium (Proc. Soc. Exp. Biol. Med., Vol. 73, p. 1, 1950) chemical defined medium (for example, CD-CHO (Invitrogen)) and the like containing about 5% to 20% fetal bovine serum can be used as the medium. The pH of the medium is preferably about 6 to 8, culture is normally performed at about 30° C. to 40° C. for about 15 to 72 hours, and aeration or agitation may be performed as necessary. When the host is an insect cell, for example, Grace's medium serum (Proc. Natl. Acad. Sci. USA, Vol. 82, p. 8404, 1985) and the like comprising fetal bovine can be mentioned, and the pH thereof is preferably about 5 to 8. Culturing is normally performed at about 20° C. to 40° C. for 15 to 100 hours, and aeration or agitation may be performed as necessary. When the host is a bacterium, an actinomyces, yeast, or a filamentous fungus, for example, a liquid medium comprising the above-described nutrient sources is appropriate. A medium having a pH of 5 to 8 is preferable. When the host is *E. coli*, preferred examples of the medium include LB medium, M9 medium (Miller et al., Exp. Mol. Genet, Cold Spring Harbor Laboratory, p. 431, 1972) and the like. In this case, culture can be normally performed at 14° C. to 43° C. for about 3 to 24 hours, while aeration or agitation is performed as necessary. When the host is a bacterium of the genus *Bacillus*, cultivation can be normally performed at 30° C. to 40° C. for about 16 to 96 hours, while aeration or agitation is performed as necessary. When the host is yeast, examples of the medium include Burkholder's minimal medium (Bostian, Proc. Natl. Acad. Sci. USA, Vol. 77, p. 4505, 1980), and the pH of the medium is desirably 5 to 8. Culturing is normally performed at about 20° C. to 35° C. for about 14 to 144 hours, and aeration or agitation may be performed as necessary.

The anti-human IL-23R antibody of the present invention can be recovered, preferably isolated and purified, from a cultured transformant as described above. Examples of the method of isolation and purification include methods based on differences in solubility, such as salting-out and solvent precipitation; methods based on differences in molecular weight, such as dialysis, ultrafiltration, gel filtration, and sodium dodecyl sulfate-polyacrylamide gel electrophoresis; methods based on differences in electric charge, such as ion exchange chromatography and hydroxyl apatite chromatography; methods based on specific affinity, such as affinity chromatography; methods based on differences in hydrophobicity, such as reverse phase high performance liquid chromatography; methods based on differences in isoelectric point, such as isoelectric focusing; and the like.

Although the present invention has been generally described above, specific examples are provided herein only for a better understanding of the present invention. These examples are for illustrative purposes only and do not limit the scope of the present invention.

EXAMPLES

The procedures involving the use of a kit or a reagent and the like were performed in accordance with the attached protocol attached unless otherwise stated.

Example 1

Preparation of Human and Monkey IL-23R-Mouse Fc Fusion Proteins

The present inventors created a fusion protein of the extracellular region sequence of a human IL-23R sequence (non-patent document 1, amino acids at positions 24 to 353 of SEQ ID NO:21) with the Fc region of mouse immunoglobulin (human IL-23R-mouse Fc fusion protein) in order to use the protein as an antigen and a screening material for constructing an anti-IL-23R antibody. Specifically, the extracellular region sequence of human IL-23R was amplified by PCR using the primers ED14-1 (SEQ ID NO:22) and ED14-2 (SEQ ID NO:23), and inserted into the EcoRI and BglII sites of pFUSE-mIgG2A-Fc2 (InvivoGen) that is a vector for the expression of a mouse Fc fusion protein, thereby obtaining a mouse Fc fusion IL-23R expression vector. Herein, the gene amplified by PCR included two EcoRI sites in the primer ED14-1 sequence and the human IL-23R gene sequence, but a gene fragment in which the EcoRI site in the human IL-23R was not digested was obtained by partial digestion and an agarose gel electrophoresis and inserted into the expression vector. The constructed vector was introduced into FreeStyle 293 cells (Invitrogen) using 293 fectin (Invitrogen) that is a gene introduction reagent, and the cells were cultured in a serum-free culture system using a FreeStyle 293 Expression medium (Invitrogen), after which a culture supernatant comprising the human IL-23R-mouse Fc fusion protein was collected. The protein was purified from the collected culture supernatant using a HiTrapA column (GE Healthcare Japan) and an AKTA system (GE Healthcare Japan) that is a protein purification system and used in the experiment described below. A monkey IL-23R-mouse Fc fusion protein was also obtained by the same method using the extracellular region sequence of monkey IL-23R sequence.

Example 2

Preparation of 293 Cells Expressing Human IL-23R

The present inventors obtained cells expressing human full-length IL-23R in order to use it as a cell antigen for testing the binding activity of anti-IL-23R antibody and obtaining an antibody. A human full-length IL-23R gene (non-patent document 1, the full length of SEQ ID NO:21) was amplified by PCR using the primers AA26-Fw (SEQ ID NO:24) and AA10-4 (SEQ ID NO:25), and the gene fragment was inserted into a pCR2.1-TOPO vector (Invitrogen) that is a cloning vector. After sequencing, the gene fragment was recombined with a pcDNA3.1 vector (Invitrogen) which is a vector for expression in mammalian cells. The vector was introduced into 293 cells, which are human established cultured cells, using Lipofectamine 2000 (Invitrogen). The cells were selectively cultured with G418-containing RPMI1640 medium, and then monocloned by a limiting-dilution method. Next, a clone showing high protein expression was selected by flow cytometry measurement using a fluorescent dye-labeled anti-human IL-23R antibody (R&D Systems), thereby obtaining cells expressing human IL-23R.

Example 3

Construction of Hybridoma Producing Anti-IL-23R Antibody

The present inventors immunized VelocImmune mice with the human IL-23R-Fc fusion protein or the human IL-23R-expressing cells obtained in Examples 1 and 2, respectively, together with an adjuvant causing an immune response, in order to obtain an anti-human IL-23R antibody. The mice were immunized several times and finally immunized once the blood antibody titer has increased. The spleen or lymph node and the like of the immunized mice was collected according to a normal method, and lymphocytes were collected therefrom and fused with the mouse myeloma cell SP2/0, thereby forming a hybridoma. Limiting-dilution samples of the hybridoma were prepared and subjected to monocloning. Each of the clones was subjected to scale-up culture, and then the medium was replaced with serum-free CD hybridoma medium (Invitrogen), followed by culturing for 5 days. The antibody was purified from the obtained culture supernatant using a protein G spin column (Pro-Chem).

Example 4

ELISA Assay

The present inventors used an antigen ELISA to measure the antigen-specific binding activity of the antibody. The human or monkey IL-23R-Fc fusion protein was immobilized onto a Maxisorp 384-well plate (Nunc, Inc.) at a concentration of 500 ng/mL. A blocking agent (Blocking One; Nacalai Tesque, Inc.) was added thereto and allowed to stand at room temperature for 1 hour, followed by washing twice with a wash buffer [TPBS: a phosphate buffered saline (PBS) containing 0.05% Tween-20], and the purified antibody samples were suitably serially diluted and added thereto. Incubation was performed at room temperature for 1 hour, followed by washing four times with TPBS, and HRP-rabbit anti-mouse Ig antibody (DAKO) which was 2000-fold diluted with a dilution buffer (Blocking One which was two-fold diluted with PBS) was added. Incubation was performed at room temperature for 1 hour, followed by washing four times with a wash buffer. 40 µL of BM-chemiluminescence ELISA substrate (POD) (Roche Diagnostics), which is a reagent for detecting chemical luminescence, was added, and the amount of chemiluminescence was measured with an EnVision counter (Perkin Elmer). Each antibody was tested in duplicate and the EC50 was analyzed by curve fitting. In this test, a fusion antibody obtained by replacing the Fc region of the humanized anti-human IL-23R antibody hum20D7 (patent document 1) with the mouse Fc region (hereinafter referred to as hum20D7-mFc) was used as a comparative antibody. Also, the reason why the hum20D7 was fused with the mouse Fc region to prepare a fusion antibody was to use anti-mouse Ig antibody as secondary antibody, and the mouse Fc region could be recognized by the anti-mouse Ig antibody, thereby rendering it possible to measure activity.

As a result, it was found that antibody (chimeric antibody) named 25-3 had high binding activity for human IL-23R, like hum20D7-mFc (Table 1). Also, regarding binding to monkey IL-23R, hum20D7-mFc showed no binding activity for monkey IL-23R, whereas 25-3 showed high binding activity for monkey IL-23R (Table 2).

TABLE 1

Binding activities of anti-human
IL-23R antibody for human IL-23R

| Antibody name | EC50 (ng/mL) |
|---|---|
| 25-3 (chimeric) | 21 |
| hum20D7-mFc | 14 |

TABLE 2

Binding activities of anti-human
IL-23R antibody for monkey IL-23R

| Antibody name | EC50 (ng/mL) |
|---|---|
| 25-3 (chimeric) | 28 |
| hum20D7-mFc | >10000 |

Example 5

Determination of Sequences of Antibody

For the antibody 25-3 identified by the above-described assay, the present inventors cloned genes encoding the heavy chain and light chain of the antibody from the hybridomas. RNA was extracted from each of the hybridomas and converted into cDNA using a cDNA amplification kit (SMARTer RACE cDNA Amplification kit; Clontech). Then, the heavy-chain and light-chain variable regions were extended and amplified by PCR. The PCR products were directly sequenced by a sequencer (ABI PRISM 3100; Applied Biosystems). Also, the PCR products were recombined with a PCR product subcloning vector such as pCR3.1-TOPO (Invitrogen), and then the gene sequences thereof were analyzed, thereby determining the sequences thereof.

The determined base sequence of the heavy-chain variable region of 25-3 is shown by SEQ ID NO:1, and the amino acid sequence thereof is shown by SEQ ID NO:2. The base sequence of the light-chain variable region of 25-3 is shown by SEQ ID NO:5, and the amino acid sequence thereof is shown by SEQ ID NO:6.

Example 6

Construction of Fully Human Antibody

The variable region of the above-described antibody is derived from humans, and the constant region thereof is derived from mice. Thus, the present inventors constructed expression vectors comprising both the heavy-chain and light-chain genes using a GS vector (Lonza Biologics) and constructed fully human antibody. Specifically, a signal sequence was linked to the 5' side of the heavy-chain variable region gene of the antibody, and the constant region gene of human Igγ1 [Man Sung Co et al., (1992) J Immunol. Vol. 148(4): 1149-1154] was linked to the 3' side, and the heavy-chain gene were inserted into the GS vector pEE6.4. Also, a signal sequence was linked to the 5' side of the light-chain variable region of the antibody, and the constant region gene of a human κ chain (Man Sung Co et al. as mentioned above) was linked to the 3' side, and the light chain genes were inserted into the GS vector pEE 12.4.

The base sequence of the heavy chain of the constructed fully human antibody of 25-3 (fully human 25-3) is shown by SEQ ID NO:3, and the amino acid sequence thereof is shown by SEQ ID NO:4. The base sequence of the light chain of the antibody is shown by SEQ ID NO:7, and the amino acid sequence thereof is shown by SEQ ID NO:8.

Example 7

Construction of Variants of the Fully Human Antibody

Furthermore, the present inventors introduced amino acid mutations into the heavy chain variable region and/or light chain variable region of the above-described fully human 25-3 to make four variants of the antibody (each was called fully human 25-3-1, fully human 25-3-2, fully human 25-3-3, fully human 25-3-4).

The base sequence of the heavy-chain variable region of the constructed fully human 25-3-1 is shown by SEQ ID NO:9, and the amino acid sequence thereof is shown by SEQ ID NO:10. The base sequence of the light-chain variable region of the antibody is shown by SEQ ID NO:5, and the amino acid sequence thereof is shown by SEQ ID NO:6. The base sequence of the heavy chain of fully human 25-3-1 is shown by SEQ ID NO:11, and the amino acid sequence thereof is shown by SEQ ID NO:12. The base sequence of the light chain of the antibody is shown by SEQ ID NO:7, and the amino acid sequence thereof is shown by SEQ ID NO:8.

The base sequence of the heavy-chain variable region of the constructed fully human 25-3-2 is shown by SEQ ID NO:9, and the amino acid sequence thereof is shown by SEQ ID NO:10. The base sequence of the light-chain variable region of the antibody is shown by SEQ ID NO:17, and the amino acid sequence thereof is shown by SEQ ID NO:18. The base sequence of the heavy chain of fully human 25-3-2 is shown by SEQ ID NO:11, and the amino acid sequence thereof is shown by SEQ ID NO:12. The base sequence of the light chain of the antibody is shown by SEQ ID NO:19, and the amino acid sequence thereof is shown by SEQ ID NO:20.

The base sequence of the heavy-chain variable region of the constructed fully human 25-3-3 is shown by SEQ ID NO:13, and the amino acid sequence thereof is shown by SEQ ID NO:14. The base sequence of the light-chain variable region of the antibody is shown by SEQ ID NO:5, and the amino acid sequence thereof is shown by SEQ ID NO:6. The base sequence of the heavy chain of fully human 25-3-3 is shown by SEQ ID NO:15, and the amino acid sequence thereof is shown by SEQ ID NO:16. The base sequence of the light chain of the antibody is shown by SEQ ID NO:7, and the amino acid sequence thereof is shown by SEQ ID NO:8.

The base sequence of the heavy-chain variable region of the constructed fully human 25-3-4 is shown by SEQ ID NO:13, and the amino acid sequence thereof is shown by SEQ ID NO:14. The base sequence of the light-chain variable region of the antibody is shown by SEQ ID NO:17, and the amino acid sequence thereof is shown by SEQ ID NO:18. The base sequence of the heavy chain of fully human 25-3-4 is shown by SEQ ID NO:15, and the amino acid sequence thereof is shown by SEQ ID NO:16. The base sequence of the light chain of the antibody is shown by SEQ ID NO:19, and the amino acid sequence thereof is shown by SEQ ID NO:20.

Example 8

Expression and Purification of the Fully Human Antibody

Using the above-described GS vectors inserted with the heavy-chain and light-chain genes of each of the antibodies, respectively, the expression of the antibodies was performed by constitutive expression. For constitutive expression, the above-described GS vectors inserted with the heavy-chain and light-chain genes of each of the antibodies, respectively, were digested with the restriction enzymes NotI and PvuI and ligated to each other using Ligation-Convenience Kit (NIPPONGENE) or Ligation-high (TOYOBO), thereby constructing GS vectors in which both the heavy-chain and light-chain genes were inserted. The expression vectors encode the full-length heavy chain and light chain and glutamine synthetase, and the antibodies were expressed by transfection in CHO-K1SV cells. The culture supernatants were purified using a protein A or protein G column (GE Healthcare Japan), thereby obtaining a purified antibody of each of the fully human antibodies.

Example 9

ELISA Assay of the Fully Human Antibodies

The present inventors used an antigen ELISA to measure the antigen-specific binding activities of the fully human antibodies constructed in the above-described Example. A human or monkey IL-23R-Fc fusion protein was immobilized onto a Maxisorp 384-well plate (Nunc, Inc.) at a concentration of 500 ng/mL. A blocking agent (Blocking One; Nacalai Tesque, Inc.) was added thereto and allowed to stand at room temperature for 1 hour, followed by washing twice with a wash buffer [TPBS: 0.05% Tween-20-containing phosphate buffered saline (PBS)], and each of the purified antibody samples was suitably serially diluted and added thereto. Incubation was performed at room temperature for 1 hour, followed by washing four times with TPBS, and HRP-labeled anti-human IgG antibody (DAKO) which was 2000-fold diluted with dilution buffer (Blocking One which was two-fold diluted with PBS) was added as secondary antibody. Incubation was performed at room temperature for 1 hour, followed by washing four times with a washing buffer. 40μL of BM-chemiluminescence ELISA substrate (POD) (Roche Diagnostics) that is a reagent for detecting chemiluminescence was added thereto and the amount of chemiluminescence was measured with an EnVision counter (Perkin Elmer). Each of the antibodies was tested in duplicate, and the EC 50 was analyzed by curve fitting.

As a result, it was found that the fully human antibody of the present invention made in the above-described Example had high binding activity for human IL-23R (Table 3). Also, regarding binding to monkey IL-23R, it was found that hum20D7 showed no binding activity for monkey IL-23R, whereas the fully human antibodies of the present invention all had high binding activity for monkey IL-23R (Table 4).

TABLE 3

Binding activities of fully human anti-human IL-23R antibodies for human IL-23R

| Antibody name | EC50 (ng/mL) |
| --- | --- |
| fully human 25-3 | 19.04 |
| fully human 25-3-1 | 17.57 |
| fully human 25-3-2 | 16.38 |
| fully human 25-3-3 | 22.07 |
| fully human 25-3-4 | 22.28 |
| hum20D7 | 45.24 |

TABLE 4

Binding activities of fully human anti-human IL-23R antibodies for monkey IL-23R

| Antibody name | EC50 (ng/mL) |
| --- | --- |
| fully human 25-3 | 12.35 |
| fully human 25-3-1 | 12.41 |
| fully human 25-3-2 | 12.23 |
| fully human 25-3-3 | 12.12 |
| fully human 25-3-4 | 12.13 |
| hum20D7 | >10000 |

Example 10

Assay for Inhibition of Human IL-23-Inducible Kit-225 Cell Proliferation

The present inventors investigated cell proliferation inhibitory activity by using Kit-225 cells (non-patent document 1) which proliferate in response to IL-23 in order to measure the antigen-specific neutralizing activities of the fully human antibodies. In this assay, Kit-225 cells subcultured in the presence of IL-2 were washed three times with RPMI 1640 containing 10% FBS and 1% penicillin/streptomycin to remove IL-2, and then a cell suspension having a cell concentration of 75000 cells/mL was prepared with the same medium and dispensed into a 96-well plate at 100 μL/well. Four-fold dilution series of the purified antibody samples were prepared with the same medium up to 2000 ng/mL, and the dilution was added to the cells and stirred with a plate mixer. Human IL-23 (Humanzyme) was added to a final concentration of 2 ng/mL, stirred and then incubated at 37° C. under 5% $CO_2$ for 5 days. Groups containing only the medium in place of the antibody sample were set as control groups, in which an IL-23-containing group was used as a 100% control, and a non-IL-23-containing group was used as a 0% control. Then, quantification was performed using Cell-Titer-Glo (Promega) which is a reagent for measuring the number of proliferated cells, and the IC50 value was analyzed by curve fitting.

As a result, it could be seen that all the fully human antibodies of the present invention had high neutralizing activity against human IL-23-inducible cell proliferation compared to hum20D7 (Table 5).

TABLE 5

Human IL-23-inducible Kit-225 cell proliferation inhibitory activities of fully human anti-human IL-23R antibodies

| Antibody name | IC50 (ng/mL) |
| --- | --- |
| fully human 25-3 | 2.25 |
| fully human 25-3-1 | 3.09 |
| fully human 25-3-2 | 2.66 |
| fully human 25-3-3 | 5.68 |
| fully human 25-3-4 | 3.48 |
| hum20D7 | 27.6 |

INDUSTRIAL APPLICABILITY

The anti-human IL-23R antibodies of the present invention are useful for the prevention or treatment of various diseases in which human IL-23 is involved in disease pathology.

The invention claimed is:

1. An anti-human interleukin-23 receptor (IL-23R) antibody or an anti-human IL-23R antibody fragment selected from any one of the following (a) to (d):
  (a) an anti-human IL-23R antibody or an anti-human IL-23R antibody fragment comprising a heavy-chain variable region consisting of the amino acid sequence shown by SEQ ID NO:10 and a light-chain variable region consisting of the amino acid sequence shown by SEQ ID NO:18;
  (b) an anti-human IL-23R antibody or an anti-human IL-23R antibody fragment comprising a heavy-chain variable region consisting of the amino acid sequence shown by SEQ ID NO:10 and a light-chain variable region consisting of the amino acid sequence shown by SEQ ID NO:6;
  (c) an anti-human IL-23R antibody or an anti-human IL-23R antibody fragment comprising a heavy-chain variable region consisting of the amino acid sequence shown by SEQ ID NO:14 and a light-chain variable region consisting of the amino acid sequence shown by SEQ ID NO:6; and
  (d) an anti-human IL-23R antibody or an anti-human IL-23R antibody fragment comprising a heavy-chain variable region consisting of the amino acid sequence shown by SEQ ID NO:14 and a light-chain variable region consisting of the amino acid sequence shown by SEQ ID NO:18.

2. The anti-human IL-23R antibody or the anti-human IL-23R antibody fragment of claim 1, comprising the heavy-chain variable region consisting of the amino acid sequence shown by SEQ ID NO:10 and the light-chain variable region consisting of the amino acid sequence shown by SEQ ID NO:18.

3. The anti-human IL-23R antibody of claim 2, comprising a heavy chain consisting of the amino acid sequence shown by SEQ ID NO:12 and a light chain consisting of the amino acid sequence shown by SEQ ID NO:20.

4. The anti-human IL-23R antibody or the anti-human IL-23R antibody fragment of claim 1, comprising the heavy-chain variable region consisting of the amino acid sequence shown by SEQ ID NO:10 and the light-chain variable region consisting of the amino acid sequence shown by SEQ ID NO:6.

5. The anti-human IL-23R antibody of claim 4, comprising a heavy chain consisting of the amino acid sequence shown by SEQ ID NO:12 and a light chain consisting of the amino acid sequence shown by SEQ ID NO:8.

6. The anti-human IL-23R antibody or the anti-human IL-23R antibody fragment of claim 1, comprising the heavy-chain variable region consisting of the amino acid sequence shown by SEQ ID NO:14 and the light-chain variable region consisting of the amino acid sequence shown by SEQ ID NO:6.

7. The anti-human IL-23R antibody of claim 6, comprising a heavy chain consisting of the amino acid sequence shown by SEQ ID NO:16 and a light chain consisting of the amino acid sequence shown by SEQ ID NO:8.

8. The anti-human IL-23R antibody or the anti-human IL-23R antibody fragment of claim 1, comprising the heavy-chain variable region consisting of the amino acid sequence shown by SEQ ID NO:14 and the light-chain variable region consisting of the amino acid sequence shown by SEQ ID NO:18.

9. The anti-human IL-23R antibody of claim 8, comprising a heavy chain consisting of the amino acid sequence shown by SEQ ID NO:16 and a light chain consisting of the amino acid sequence shown by SEQ ID NO:20.

10. The anti-human IL-23R antibody or the anti-human IL-23R antibody fragment of claim 1, wherein the heavy-chain constant region of the antibody or the antibody fragment is a human Igγ1 constant region.

11. The anti-human IL-23R antibody or the anti-human IL-23R antibody fragment of claim 1, wherein the light-chain constant region of the antibody or the antibody fragment is a human Igκ constant region.

12. The anti-human IL-23R antibody or the anti-human IL-23R antibody fragment of claim 1, wherein the heavy-chain constant region of the antibody or the antibody fragment is a human Igγ1 constant region, and the light-chain constant region of the antibody or antibody fragment is a human Igκ constant region.

13. The antibody fragment of claim 1, wherein the fragment is a single-chain variable region fragment, Fab, Fab', or F(ab')$_2$.

14. The antibody fragment of claim 13, wherein the fragment is fused with another peptide or protein, or is modified with a modifying agent selected from polyethylene glycol, a sugar chain, and a phospholipid.

15. A polynucleotide comprising a sequence encoding the heavy-chain variable region of the antibody or the antibody fragment of claim 1.

16. A polynucleotide comprising a sequence encoding the light-chain variable region of the antibody or the antibody fragment of claim 1.

17. An expression vector comprising a polynucleotide comprising a sequence encoding the heavy-chain variable region of the antibody or the antibody fragment of claim 1 and/or a polynucleotide comprising a sequence encoding the light-chain variable region of the antibody or the antibody fragment of claim 1.

18. A cultured host cell which is selected from the group consisting of the following (a) and (b):
   (a) a host cell transformed with an expression vector comprising a polynucleotide comprising a sequence that encodes the heavy-chain variable region of the antibody or the antibody fragment of claim 1 and a polynucleotide comprising a sequence that encodes the light-chain variable region of the antibody or the antibody fragment of claim 1; and
   (b) a host cell transformed with an expression vector comprising a polynucleotide comprising a sequence that encodes the heavy-chain variable region of the antibody or the antibody fragment of claim 1 and an expression vector comprising a polynucleotide comprising a sequence that encodes the light-chain variable region of the antibody or the antibody fragment of claim 1.

19. A method for producing an anti-human IL-23R antibody or an anti-human IL-23R antibody fragment, the method comprising a step of culturing the host cell of claim 18 and expressing an anti-human IL-23R antibody or an antibody fragment under conditions suitable for the production of the antibody or the antibody fragment.

20. An anti-human IL-23R antibody or an anti-human IL-23R antibody fragment produced by the method of claim 19.

21. The antibody fragment of claim 20, wherein the fragment is a single-chain variable region fragment, Fab, Fab', or F(ab')$_2$.

22. The antibody fragment of claim 21, wherein the fragment is fused with another peptide or protein, or is modified with a modifying agent selected from polyethylene glycol, a sugar chain, and a phospholipid.

23. A cultured host cell which is selected from the group consisting of the following (a) and (b):
   (a) a host cell transformed with an expression vector comprising a polynucleotide comprising a sequence that encodes the heavy chain of the antibody of any one of claims 9 to 12 and a polynucleotide comprising a sequence that encodes the light chain of the antibody; and
   (b) a host cell transformed with an expression vector comprising a polynucleotide comprising a sequence that encodes the heavy chain of the antibody of any one of claims 9 to 12 and an expression vector comprising a polynucleotide comprising a sequence that encodes the light chain of the antibody.

24. A method for producing an anti-human IL-23R antibody, the method comprising a step of culturing the host cell of claim 23 and expressing an anti-human IL-23R antibody under conditions suitable for the production of the antibody.

25. An anti-human IL-23R antibody produced by the method of claim 24.

* * * * *

SEQUENCE LISTING

<160> NUMBER OF SEQ ID NOS: 25

<210> SEQ ID NO 1
<211> LENGTH: 357
<212> TYPE: DNA
<213> ORGANISM: Artificial Sequence
<220> FEATURE:
<223> OTHER INFORMATION: VH gene of anti-human IL-23R antibody

<400> SEQUENCE: 1
caggtgcagc tgcaggagtc gggcccagga caggtgaagc cttcacagac cctgtccctc      60
acctgctctg tctctggtgg ctccatcgac agtggtgatc actactggac ctggatccgc     120
caacaccctg gggaggtcct ggagtggatt ggctacatct attccagtgg cacacctac      180 tacagcccgt ccctcaagag tcgacttacc atgtcattag acacgtctaa gaaccagttc     240
tccctgaggc tgagctctgt gactgccgcg gacacggccg tttattactg tgcgagagtt     300
ggtgactacg agtggttcga cacctggggc cagggaaccc tggtcaccgt ctcctca       357

<210> SEQ ID NO 2
<211> LENGTH: 119
<212> TYPE: PRT
<213> ORGANISM: Artificial Sequence
<220> FEATURE:
<223> OTHER INFORMATION: VH of anti-human IL-23R antibody

<400> SEQUENCE: 2

Gln Val Gln Leu Gln Glu Ser Gly Pro Gly Gln Val Lys Pro Ser Gln
1               5                   10                  15

Thr Leu Ser Leu Thr Cys Ser Val Ser Gly Gly Ser Ile Asp Ser Gly
            20                  25                  30

Asp His Tyr Trp Thr Trp Ile Arg Gln His Pro Gly Glu Val Leu Glu
        35                  40                  45

Trp Ile Gly Tyr Ile Tyr Ser Ser Gly His Thr Tyr Tyr Ser Pro Ser
    50                  55                  60

Leu Lys Ser Arg Leu Thr Met Ser Leu Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Val Gly Asp Tyr Glu Trp Phe Asp Thr Trp Gly Gln Gly
            100                 105                 110

Thr Leu Val Thr Val Ser Ser
        115

<210> SEQ ID NO 3
<211> LENGTH: 1350
<212> TYPE: DNA
<213> ORGANISM: Artificial Sequence
<220> FEATURE:
<223> OTHER INFORMATION: H-chain gene of anti-human IL-23R antibody

<400> SEQUENCE: 3
caggtgcagc tgcaggagtc gggcccagga caggtgaagc cttcacagac cctgtccctc      60
acctgctctg tctctggtgg ctccatcgac agtggtgatc actactggac ctggatccgc     120
caacaccctg gggaggtcct ggagtggatt ggctacatct attccagtgg cacacctac      180 tacagcccgt ccctcaagag tcgacttacc atgtcattag acacgtctaa gaaccagttc     240
tccctgaggc tgagctctgt gactgccgcg gacacggccg tttattactg tgcgagagtt     300
ggtgactacg agtggttcga cacctggggc cagggaaccc tggtcaccgt ctcctcagcc     360

```
tccaccaagg gcccatcggt cttcccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc ttagtagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350
```

<210> SEQ ID NO 4
<211> LENGTH: 449
<212> TYPE: PRT
<213> ORGANISM: Artificial Sequence
<220> FEATURE:
<223> OTHER INFORMATION: H-chain of anti-human IL-23R antibody

<400> SEQUENCE: 4

```
Gln Val Gln Leu Gln Glu Ser Gly Pro Gly Val Lys Pro Ser Gln
1               5                   10                  15

Thr Leu Ser Leu Thr Cys Ser Val Ser Gly Gly Ser Ile Asp Ser Gly
                20                  25                  30

Asp His Tyr Trp Thr Trp Ile Arg Gln His Pro Gly Glu Val Leu Glu
            35                  40                  45

Trp Ile Gly Tyr Ile Tyr Ser Ser Gly His Thr Tyr Tyr Ser Pro Ser
        50                  55                  60

Leu Lys Ser Arg Leu Thr Met Ser Leu Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Val Gly Asp Tyr Glu Trp Phe Asp Thr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                180             185                 190
Ser Ser Leu Gly Thr Gln Thr Tyr Ile Cys Asn Val Asn His Lys Pro
        195                 200             205
Ser Asn Thr Lys Val Asp Lys Lys Val Glu Pro Lys Ser Cys Asp Lys
        210                 215             220
Thr His Thr Cys Pro Pro Cys Pro Ala Pro Glu Leu Leu Gly Gly Pro
225             230                 235             240
Ser Val Phe Leu Phe Pro Pro Lys Pro Lys Asp Thr Leu Met Ile Ser
            245                 250             255
Arg Thr Pro Glu Val Thr Cys Val Val Val Asp Val Ser His Glu Asp
            260                 265             270
Pro Glu Val Lys Phe Asn Trp Tyr Val Asp Gly Val Glu Val His Asn
        275                 280             285
Ala Lys Thr Lys Pro Arg Glu Glu Gln Tyr Asn Ser Thr Tyr Arg Val
        290                 295             300
Val Ser Val Leu Thr Val Leu His Gln Asp Trp Leu Asn Gly Lys Glu
305             310                 315             320
Tyr Lys Cys Lys Val Ser Asn Lys Ala Leu Pro Ala Pro Ile Glu Lys
            325                 330             335
Thr Ile Ser Lys Ala Lys Gly Gln Pro Arg Glu Pro Gln Val Tyr Thr
            340                 345             350
Leu Pro Pro Ser Arg Asp Glu Leu Thr Lys Asn Gln Val Ser Leu Thr
            355                 360             365
Cys Leu Val Lys Gly Phe Tyr Pro Ser Asp Ile Ala Val Glu Trp Glu
        370                 375             380
Ser Asn Gly Gln Pro Glu Asn Asn Tyr Lys Thr Thr Pro Pro Val Leu
385             390                 395             400
Asp Ser Asp Gly Ser Phe Phe Leu Tyr Ser Lys Leu Thr Val Asp Lys
                405                 410             415
Ser Arg Trp Gln Gln Gly Asn Val Phe Ser Cys Ser Val Met His Glu
            420                 425             430
Ala Leu His Asn His Tyr Thr Gln Lys Ser Leu Ser Leu Ser Pro Gly
        435                 440             445
Lys

<210> SEQ ID NO 5
<211> LENGTH: 342
<212> TYPE: DNA
<213> ORGANISM: Artificial Sequence
<220> FEATURE:
<223> OTHER INFORMATION: VL gene of anti-human IL-23R antibody

<400> SEQUENCE: 5
gacatcgtga tgacccagtc tccagactcc ctggctgtgt cactgggcga gagggccacc        60
atcaactgca gtccagcca gactatttta taccctcca ataatatgaa ttacttaggt        120
tggtaccagc agagagcagg acagtctcct aggctgctca tttactgggc atctacccgg       180
gaatccgggg tccctgaccg attcagtggc agcgggtctg ggacagattt cactcttacc       240
atcagcagcc tgcaggctga agatgtggca gtttattact gtcaacaata ttatagtagt       300
cttccgacgt tcggccaagg gaccaaggtg gaaatcaaac gg                          342

<210> SEQ ID NO 6
<211> LENGTH: 114
<212> TYPE: PRT
<213> ORGANISM: Artificial Sequence
```

<220> FEATURE:
<223> OTHER INFORMATION: VL of anti-human IL-23R antibody

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Ile Leu Tyr Pro
            20                  25                  30

Ser Asn Asn Met Asn Tyr Leu Gly Trp Tyr Gln Gln Arg Ala Gly Gln
        35                  40                  45

Ser Pro Arg Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Leu Pro Thr Phe Gly Gln Gly Thr Lys Val Glu Ile
            100                 105                 110

Lys Arg

<210> SEQ ID NO 7
<211> LENGTH: 663
<212> TYPE: DNA
<213> ORGANISM: Artificial Sequence
<220> FEATURE:
<223> OTHER INFORMATION: L-chain gene of anti-human IL-23R antibody

<400> SEQUENCE: 7
gacatcgtga tgacccagtc tccagactcc ctggctgtgt cactgggcga gagggccacc     60
atcaactgca agtccagcca gactatttta taccctccca ataatatgaa ttacttaggt    120
tggtaccagc agagagcagg acagtctcct aggctgctca tttactgggc atctacccgg    180
gaatccgggg tccctgaccg attcagtggc agcgggtctg ggacagattt cactcttacc    240
atcagcagcc tgcaggctga agatgtggca gtttattact gtcaacaata ttatagtagt    300
cttccgacgt tcggccaagg gaccaaggtg gaaatcaaac ggactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaagt ctacgcctgc    600
gaagtcaccc atcagggcct gagctcgccc gtcacaaaga gcttcaacag gggagagtgt    660
tag                                                                  663

<210> SEQ ID NO 8
<211> LENGTH: 220
<212> TYPE: PRT
<213> ORGANISM: Artificial Sequence
<220> FEATURE:
<223> OTHER INFORMATION: L-chain of anti-human IL-23R antibody

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Ile Leu Tyr Pro
            20                  25                  30

Ser Asn Asn Met Asn Tyr Leu Gly Trp Tyr Gln Gln Arg Ala Gly Gln

```
                35                  40                  45
Ser Pro Arg Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Leu Pro Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 9
<211> LENGTH: 357
<212> TYPE: DNA
<213> ORGANISM: Artificial Sequence
<220> FEATURE:
<223> OTHER INFORMATION: VH gene of anti-human IL-23R antibody

<400> SEQUENCE: 9
caggtgcagc tgcaggagtc gggcccagga ctggtgaagc cttcacagac cctgtccctc      60
acctgctctg tctctggtgg ctccatcgac agtggtgatc actactggac ctggatccgc     120 caaaccctg ggaagggcct ggagtggatt ggctacatct attccagtgg cacacctac      180 tacagcccgt ccctcaagag tcgagtgacc atctcagtgg acacgtctaa gaaccagttc     240
tccctgaggc tgagctctgt gactgccgcg gacacggccg tttattactg tgcgagagtt     300
ggtgactacg agtggttcga cacctggggc cagggaaccc tggtcaccgt ctcctca        357

<210> SEQ ID NO 10
<211> LENGTH: 119
<212> TYPE: PRT
<213> ORGANISM: Artificial Sequence
<220> FEATURE:
<223> OTHER INFORMATION: VH of anti-human IL-23R antibody

<400> SEQUENCE: 10

Gln Val Gln Leu Gln Glu Ser Gly Pro Gly Leu Val Lys Pro Ser Gln
1               5                   10                  15

Thr Leu Ser Leu Thr Cys Ser Val Ser Gly Gly Ser Ile Asp Ser Gly
            20                  25                  30

Asp His Tyr Trp Thr Trp Ile Arg Gln His Pro Gly Lys Gly Leu Glu
            35                  40                  45

Trp Ile Gly Tyr Ile Tyr Ser Ser Gly His Thr Tyr Tyr Ser Pro Ser
    50                  55                  60
```

Leu Lys Ser Arg Val Thr Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Val Gly Asp Tyr Glu Trp Phe Asp Thr Trp Gly Gln Gly
            100                 105                 110

Thr Leu Val Thr Val Ser Ser
        115

<210> SEQ ID NO 11
<211> LENGTH: 1350
<212> TYPE: DNA
<213> ORGANISM: Artificial Sequence
<220> FEATURE:
<223> OTHER INFORMATION: H-chain gene of anti-human IL-23R antibody

<400> SEQUENCE: 11
caggtgcagc tgcaggagtc gggcccagga ctggtgaagc cttcacagac cctgtccctc      60
acctgctctg tctctggtgg ctccatcgac agtggtgatc actactggac ctggatccgc     120
caacaccctg ggaagggcct ggagtggatt ggctacatct attccagtgg cacacctac     180
tacagcccgt ccctcaagag tcgagtgacc atctcagtgg acacgtctaa gaaccagttc     240
tccctgaggc tgagctctgt gactgccgcg gacacggccg tttattactg tgcgagagtt     300
ggtgactacg agtggttcga cacctggggc cagggaaccc tggtcaccgt ctcctcagcc     360
tccaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc ttagtagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350

<210> SEQ ID NO 12
<211> LENGTH: 449
<212> TYPE: PRT
<213> ORGANISM: Artificial Sequence
<220> FEATURE:
<223> OTHER INFORMATION: H-chain of anti-human IL-23R antibody

<400> SEQUENCE: 12

Gln Val Gln Leu Gln Glu Ser Gly Pro Gly Leu Val Lys Pro Ser Gln

-continued

```
1               5                   10                  15
Thr Leu Ser Leu Thr Cys Ser Val Ser Gly Gly Ser Ile Asp Ser Gly
                20                  25                  30
Asp His Tyr Trp Thr Trp Ile Arg Gln His Pro Gly Lys Gly Leu Glu
                35                  40                  45
Trp Ile Gly Tyr Ile Tyr Ser Ser Gly His Thr Tyr Tyr Ser Pro Ser
                50                  55                  60
Leu Lys Ser Arg Val Thr Ile Ser Val Asp Thr Ser Lys Asn Gln Phe
65                  70                  75                  80
Ser Leu Arg Leu Ser Ser Val Thr Ala Ala Asp Thr Ala Val Tyr Tyr
                85                  90                  95
Cys Ala Arg Val Gly Asp Tyr Glu Trp Phe Asp Thr Trp Gly Gln Gly
                100                 105                 110
Thr Leu Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
                130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
```

Ala Leu His Asn His Tyr Thr Gln Lys Ser Leu Ser Leu Ser Pro Gly
        435                 440                 445

Lys

<210> SEQ ID NO 13
<211> LENGTH: 357
<212> TYPE: DNA
<213> ORGANISM: Artificial Sequence
<220> FEATURE:
<223> OTHER INFORMATION: VH gene of anti-human IL-23R antibody

<400> SEQUENCE: 13
caggtgcagc tgcaggagtc gggcccagga ctggtgaagc cttcacagac cctgtccctc    60
acctgctctg tctctggtgg ctccatcagc agtggtgatc actactggac ctggatccgc   120
caacaccctg gaagggcct ggagtggatt ggctacatct attccagtgg gcacacctac    180
tacagcccgt ccctcaagag tcgagtgacc atctcagtgg acacgtctaa gaaccagttc   240
tccctgaggc tgagctctgt gactgccgcg gacacggccg tttattactg tgcgagagtt   300
ggtgactacg agtggttcga cacctggggc cagggaaccc tggtcaccgt ctcctca     357

<210> SEQ ID NO 14
<211> LENGTH: 119
<212> TYPE: PRT
<213> ORGANISM: Artificial Sequence
<220> FEATURE:
<223> OTHER INFORMATION: VH of anti-human IL-23R antibody

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Ser Val Ser Gly Gly Ser Ile Ser Ser Gly
            20                  25                  30

Asp His Tyr Trp Thr Trp Ile Arg Gln His Pro Gly Lys Gly Leu Glu
        35                  40                  45

Trp Ile Gly Tyr Ile Tyr Ser Ser Gly His Thr Tyr Tyr Ser Pro Ser
    50                  55                  60

Leu Lys Ser Arg Val Thr Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Val Gly Asp Tyr Glu Trp Phe Asp Thr Trp Gly Gln Gly
            100                 105                 110

Thr Leu Val Thr Val Ser Ser
        115

<210> SEQ ID NO 15
<211> LENGTH: 1350
<212> TYPE: DNA
<213> ORGANISM: Artificial Sequence
<220> FEATURE:
<223> OTHER INFORMATION: H-chain gene of anti-human IL-23R antibody

<400> SEQUENCE: 15
caggtgcagc tgcaggagtc gggcccagga ctggtgaagc cttcacagac cctgtccctc    60
acctgctctg tctctggtgg ctccatcagc agtggtgatc actactggac ctggatccgc   120
caacaccctg gaagggcct ggagtggatt ggctacatct attccagtgg gcacacctac    180
tacagcccgt ccctcaagag tcgagtgacc atctcagtgg acacgtctaa gaaccagttc   240

```
tccctgaggc tgagctctgt gactgccgcg gacacggccg tttattactg tgcgagagtt      300
ggtgactacg agtggttcga cacctggggc cagggaaccc tggtcaccgt ctcctcagcc      360
tccaccaagg gcccatcggt cttccccctg gcaccctcct ccaagagcac ctctgggggc      420
acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga      540
ctctactccc ttagtagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttcccccc aaaacccaag gacaccctca tgatctcccg gacccctgag      780
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc ccccatcccg ggatgagctg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaatga                                     1350
```

<210> SEQ ID NO 16
<211> LENGTH: 449
<212> TYPE: PRT
<213> ORGANISM: Artificial Sequence
<220> FEATURE:
<223> OTHER INFORMATION: H-chain of anti-human IL-23R antibody

<400> SEQUENCE: 16

```
Gln Val Gln Leu Gln Glu Ser Gly Pro Gly Leu Val Lys Pro Ser Gln
1               5                   10                  15

Thr Leu Ser Leu Thr Cys Ser Val Ser Gly Gly Ser Ile Ser Ser Gly
            20                  25                  30

Asp His Tyr Trp Thr Trp Ile Arg Gln His Pro Gly Lys Gly Leu Glu
        35                  40                  45

Trp Ile Gly Tyr Ile Tyr Ser Ser Gly His Thr Tyr Tyr Ser Pro Ser
    50                  55                  60

Leu Lys Ser Arg Val Thr Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Val Gly Asp Tyr Glu Trp Phe Asp Thr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
        180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
Lys

<210> SEQ ID NO 17
<211> LENGTH: 342
<212> TYPE: DNA
<213> ORGANISM: Artificial Sequence
<220> FEATURE:
<223> OTHER INFORMATION: VL gene of anti-human IL-23R antibody

<400> SEQUENCE: 17
gacatcgtga tgacccagtc tccagactcc ctggctgtgt cactgggcga gagggccacc      60
atcaactgca agtccagcca gactattttta taccctttca ataatatgaa ttacttaggt     120
tggtaccagc agaaaccagg acagtctcct aggctgctca tttactgggc atctacccgg     180
gaatccgggg tccctgaccg attcagtggc agcgggtctg ggacagattt cactcttacc     240
atcagcagcc tgcaggctga agatgtggca gtttattact gtcaacaata ttatagtagt     300
cttccgacgt tcggccaagg gaccaaggtg gaaatcaaac gg                         342
```

```
<210> SEQ ID NO 18
<211> LENGTH: 114
<212> TYPE: PRT
<213> ORGANISM: Artificial Sequence
<220> FEATURE:
<223> OTHER INFORMATION: VL of anti-human IL-23R antibody

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Ile Leu Tyr Pro
            20                  25                  30

Ser Asn Asn Met Asn Tyr Leu Gly Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Leu Pro Thr Phe Gly Gln Gly Thr Lys Val Glu Ile
            100                 105                 110

Lys Arg

<210> SEQ ID NO 19
<211> LENGTH: 663
<212> TYPE: DNA
<213> ORGANISM: Artificial Sequence
<220> FEATURE:
<223> OTHER INFORMATION: L-chain gene of anti-human IL-23R antibody

<400> SEQUENCE: 19
gacatcgtga tgacccagtc tccagactcc ctggctgtgt cactgggcga gagggccacc    60
atcaactgca agtccagcca gactatttta taccccttcca ataatatgaa ttacttaggt   120
tggtaccagc agaaaccagg acagtctcct aggctgctca tttactgggc atctacccgg   180
gaatccgggg tccctgaccg attcagtggc agcgggtctg ggacagattt cactcttacc   240
atcagcagcc tgcaggctga agatgtggca gtttattact gtcaacaata ttatagtagt   300
cttccgacgt tcggccaagg gaccaaggtg gaaatcaaac ggactgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaaagt ctacgcctgc   600
gaagtcaccc atcagggcct gagctcgccc gtcacaaaga gcttcaacag gggagagtgt   660
tag                                                                 663

<210> SEQ ID NO 20
<211> LENGTH: 220
<212> TYPE: PRT
<213> ORGANISM: Artificial Sequence
<220> FEATURE:
<223> OTHER INFORMATION: L-chain of anti-human IL-23R antibody

<400> SEQUENCE: 20

Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser Gln Thr Ile Leu Tyr Pro
                20                  25                  30

Ser Asn Asn Met Asn Tyr Leu Gly Trp Tyr Gln Gln Lys Pro Gly Gln
            35                  40                  45

Ser Pro Arg Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Leu Pro Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 21
<211> LENGTH: 629
<212> TYPE: PRT
<213> ORGANISM: Homo sapiens

<400> SEQUENCE: 21

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
                20                  25                  30

His Ile Trp Val Glu Pro Ala Thr Ile Phe Lys Met Gly Met Asn Ile
            35                  40                  45

Ser Ile Tyr Cys Gln Ala Ala Ile Lys Asn Cys Gln Pro Arg Lys Leu
        50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
                165                 170                 175
```

```
Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
            195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Pro Phe Phe His Lys Thr Pro Glu Thr Val Pro
305                 310                 315                 320

Gln Val Thr Ser Lys Ala Phe Gln His Asp Thr Trp Asn Ser Gly Leu
                325                 330                 335

Thr Val Ala Ser Ile Ser Thr Gly His Leu Thr Ser Asp Asn Arg Gly
            340                 345                 350

Asp Ile Gly Leu Leu Leu Gly Met Ile Val Phe Ala Val Met Leu Ser
        355                 360                 365

Ile Leu Ser Leu Ile Gly Ile Phe Asn Arg Ser Phe Arg Thr Gly Ile
    370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Glu Asn Ser
                405                 410                 415

Glu Leu Met Asn Asn Asn Ser Ser Glu Gln Val Leu Tyr Val Asp Pro
            420                 425                 430

Met Ile Thr Glu Ile Lys Glu Ile Phe Ile Pro Glu His Lys Pro Thr
        435                 440                 445

Asp Tyr Lys Lys Glu Asn Thr Gly Pro Leu Glu Thr Arg Asp Tyr Pro
    450                 455                 460

Gln Asn Ser Leu Phe Asp Asn Thr Thr Val Val Tyr Ile Pro Asp Leu
465                 470                 475                 480

Asn Thr Gly Tyr Lys Pro Gln Ile Ser Asn Phe Leu Pro Glu Gly Ser
                485                 490                 495

His Leu Ser Asn Asn Asn Glu Ile Thr Ser Leu Thr Leu Lys Pro Pro
            500                 505                 510

Val Asp Ser Leu Asp Ser Gly Asn Asn Pro Arg Leu Gln Lys His Pro
        515                 520                 525

Asn Phe Ala Phe Ser Val Ser Val Asn Ser Leu Ser Asn Thr Ile
    530                 535                 540

Phe Leu Gly Glu Leu Ser Leu Ile Leu Asn Gln Gly Glu Cys Ser Ser
545                 550                 555                 560

Pro Asp Ile Gln Asn Ser Val Glu Glu Thr Thr Met Leu Leu Glu
                565                 570                 575

Asn Asp Ser Pro Ser Glu Thr Ile Pro Glu Gln Thr Leu Leu Pro Asp
            580                 585                 590
```

Glu Phe Val Ser Cys Leu Gly Ile Val Asn Glu Leu Pro Ser Ile
            595                 600                 605

Asn Thr Tyr Phe Pro Gln Asn Ile Leu Glu Ser His Phe Asn Arg Ile
            610                 615                 620

Ser Leu Leu Glu Lys
625

<210> SEQ ID NO 22
<211> LENGTH: 42
<212> TYPE: DNA
<213> ORGANISM: Artificial Sequence
<220> FEATURE:
<223> OTHER INFORMATION: synthetic primer

<400> SEQUENCE: 22
aacatgaatt cgggaattac aaatataaac tgctctggcc ac                           42

<210> SEQ ID NO 23
<211> LENGTH: 41
<212> TYPE: DNA
<213> ORGANISM: Artificial Sequence
<220> FEATURE:
<223> OTHER INFORMATION: synthetic primer

<400> SEQUENCE: 23
actctagatc tgtctcctct gttgtcagaa gtaaggtgcc c                            41

<210> SEQ ID NO 24
<211> LENGTH: 39
<212> TYPE: DNA
<213> ORGANISM: Artificial Sequence
<220> FEATURE:
<223> OTHER INFORMATION: synthetic primer

<400> SEQUENCE: 24
caccatgaat caggtcacta ttcaatggga tgcagtaat                               39

<210> SEQ ID NO 25
<211> LENGTH: 44
<212> TYPE: DNA
<213> ORGANISM: Artificial Sequence
<220> FEATURE:
<223> OTHER INFORMATION: synthetic primer

<400> SEQUENCE: 25
acatagcggc cgcctacttt tccaagagtg aaatcctatt gaag                         44